(12) United States Patent
Maor et al.

(10) Patent No.: US 8,637,055 B2
(45) Date of Patent: Jan. 28, 2014

(54) COSMETIC COMPOSITIONS CONTAINING SMALL MAGNETIC PARTICLES

(75) Inventors: Zeev Maor, Dead Sea (IL); Michael Royz, Jerusalem (IL)

(73) Assignee: Ahava-Dead Sea Laboratories Ltd., Lod (IL)

( * ) Notice: Subject to any disclaimer, the term of this patent is extended or adjusted under 35 U.S.C. 154(b) by 1644 days.

(21) Appl. No.: 10/519,387

(22) PCT Filed: Jun. 23, 2003

(86) PCT No.: PCT/IL03/00529
§ 371 (c)(1),
(2), (4) Date: Dec. 27, 2004

(87) PCT Pub. No.: WO04/000244
PCT Pub. Date: Dec. 31, 2003

(65) Prior Publication Data
US 2005/0232955 A1    Oct. 20, 2005

Related U.S. Application Data

(60) Provisional application No. 60/390,370, filed on Jun. 24, 2002.

(51) Int. Cl.
*A61K 8/19* (2006.01)
*A61K 33/00* (2006.01)

(52) U.S. Cl.
USPC ........... 424/401; 424/600; 424/722; 514/769; 514/770

(58) Field of Classification Search
None
See application file for complete search history.

(56) References Cited

U.S. PATENT DOCUMENTS

| | | | |
|---|---|---|---|
| 4,046,591 A | 9/1977 | Laguerre | |
| 5,705,172 A | 1/1998 | Efron et al. | |
| 5,800,835 A | 9/1998 | Zastrow et al. | |
| 5,919,490 A * | 7/1999 | Zastrow et al. | 424/647 |
| 5,961,988 A | 10/1999 | Zastrow et al. | |
| 6,033,655 A | 3/2000 | Lahanas et al. | |
| 6,187,031 B1 | 2/2001 | Douglas | |
| 6,248,340 B1 | 6/2001 | Maor et al. | |
| 6,294,180 B1 | 9/2001 | Demars et al. | |
| 6,383,129 B1 | 5/2002 | Ardizzone et al. | |
| 6,582,709 B1 | 6/2003 | Maor et al. | |
| 2003/0028069 A1 | 2/2003 | Santiago | |

FOREIGN PATENT DOCUMENTS

| | | |
|---|---|---|
| CH | 313679 | 6/1956 |
| EP | 1 000 608 | 5/2000 |
| EP | 1 043 018 | 10/2000 |
| EP | 0 686 447 | 12/2005 |
| FR | 2268512 | 11/1975 |
| JP | 0 1242513 | 9/1989 |
| RU | 2 192 240 | 11/2002 |
| WO | WO 99/33443 | 7/1999 |
| WO | WO 00/40255 | * 7/2000 ............. A61K 35/02 |
| WO | WO 01/28338 | 4/2001 |
| WO | WO 01/28512 | 4/2001 |
| WO | WO 02/05891 | 1/2002 |
| WO | WO 02/053114 | 7/2002 |

OTHER PUBLICATIONS

Shiga Yoko, JP 4108710, 1990 (abstract).*
Mayrovitz et al "Assessment of the Short-Term Effects of a Permanent Magnet on Normal Skin Blood Circulation via Laser-Doppler Flowmetry", *The Scientific Review of Alternative Medicine* 6(1):9-12, 2002.
Martel et al, "Comparison of Static and Placebo Magnets on Resting Forearm Blood Flow in Young, Healthy Men", *Journal of Orthopaedic and Sports Physical Therapy*, 2002;32(10):518-524.
Saygili et al "Investigation of the Effect of Magnetic Retention Systems Used in Prostheses on Buccal Mucosal Blood Flow", *Int J. Prosthodont*, 1992;5(4):326-332.
XP-002257197, 1992, JP.
XP-002257198, 1987, JP.
XP-002257194, 1998, JP.
XP-002257195, 1989, JP.
XP-002257196, 2001, JP.
Bellossi et al "No effect of a low-frequency pulsed magnetic field on the brain blood flow among mice", *Panminerva Med*. 1993; 35(1):57-9.
Ichioka et al "Biological effects of static magnetic fields on the microcirculatory blood flow in vivo: a preliminary report", *Med. Biol. Eng. Comput*. Jan. 1998,:36(1):91-5.
Ichioka et al "High-Intensity Static Magnetic Fields Modulate Skin Microcirculation and Temperature in Vivo", *Bioelectromagnetics*, 2000; 21(3):183-8.
Collacott et al "Bipolar Permanent Magnets for the Treatment of Chronic Low Back Pain: a pilot study", *JAMA*. Mar. 8, 2000;283(10):1322-5.

* cited by examiner

*Primary Examiner* — Daniel Sullivan
*Assistant Examiner* — Barbara Frazier
(74) *Attorney, Agent, or Firm* — Vorys, Sater, Seymour and Pease LLP; Susanne M. Hopkins

(57) ABSTRACT

The present invention present a novel and cost-effective family of cosmetic compositions comprising inter alia small magnetic particles characterized by magnetic field adapted to be topically administrated adjacent to skin surface, absorbed to epidermal upper skin layers and place in a direct contact to the body, usually above pain suffering regions. The present invention also provides the use of the compositions, especially of nano-powders of salts obtained from the Dead Sea, as an external layer of bandages, dressings, compresses or warps, so constantly approached to be in an intimate contact with the patient's skin.

5 Claims, No Drawings

COSMETIC COMPOSITIONS CONTAINING SMALL MAGNETIC PARTICLES

RELATED APPLICATIONS

The present application is based on International Application No. PCT/IL2003/000529 filed Jun. 23, 2003, and claims priority from, U.S. Provisional Application No. 60/390,370, filed Jun. 24, 2002, the disclosure of which is hereby incorporated by reference herein in its entirety.

FILED OF THE INVENTION

The present invention generally relates to cosmetic compositions comprising inter alia small magnetic particles. More specifically, the present invention relates to cosmetic compositions comprising Dead Sea salts and/or biocompatible metal compositions characterized by magnetic field, adapted to be topically administrated on the skin for cosmetic or medical purposes.

BACKGROUND OF THE INVENTION

Magnet therapy is attracting more and more people, and is gaining experimental evidence for its heeling effects. The term "magnet therapy" refers to the use of static magnets attached to skin surface, absorbed to epidermal upper skin layers and place in a direct contact to the body, usually above pain suffering regions. All products in the market, aimed at providing magnet therapy, are based on creating a magnetic field by placing a static magnet, or metal having magnetic properties, on top of a part of the body which needs the treatment.

Obviously, since the source of magnetic field is presented in the form of large rigid pieces of magnets (or metals) such as disks etc., it is very difficult to achieve direct, close contact between the body and the source of magnetic field. Since strength of the magnetic field is highly affected by the length between the source and the treated area, static magnets are either attached to the body by tape or placed in specially designed products such as belts, wraps, or mattress pads. These methods have literally relief pain for many people spanning the globe. Therefore, new products in the market are available as wraps and adhesive disks, which should be placed as close as possible to the specific treated part of the body. However, such products are still not with good contact and are also limited to specific parts of the body they were designed to; for example, magnetic facial mask has a different geometry then that of a neck wrap.

Therefore, there is a need for a product, which would enable closer contact of the magnetic material, with the body, without being too limited regarding the part of body gains the treatment.

By this invention, we describe a new way to bring the magnetic material into close contact with the skin, in the form of cosmetic compositions. Such compositions are contains finely divided magnetic material, within a cosmetic preparations such as cream, gel, lotion, etc.

The cosmetic effect of magnets is recognized for a long time. For example, there are several products in the market aimed to achieve cosmetic benefits, due to the contact between the magnetic material and the skin, however, still in the form of wraps made of textile, or plastic material, in which the magnets are embedded. Such products are sold as anti-aging magnetic head/neck wrap, anti-aging facial-mask etc.

U.S. Pat. No. 6,383,129 to Ardizzone et al. discloses a magneto-therapeutic device incorporates bio-ceramic fibers, which provides simultaneous magneto-therapy and far infrared wave therapy. Similarly, Swiss Pat. No. 313679 shows a handheld massage therapy device having a rotating carrier containing multiple magnetic balls. Russian Pat. No. 2,192,240 to Aronpolin et al. introduces a method involves manual massage given simultaneously with magnet therapy. U.S. Pat. No. 2,003,028,069 to Santiago presents a bio-enhanced magnetic device for promoting hair growth by stimulating a beneficial blood circulation especially on the scalp area. WO0205891 to Ardizzone et al. introduces a magneto-therapeutic device incorporates bio-ceramic fibers which provide simultaneous magneto-therapy and far infrared wave therapy. Lastly, U.S. Pat. No. 6,187,031 to Douglas presents a magnetic pack having water absorbent filler such as poly-acrylamide and having at least one magnet and an accessory strap that allows the application of magnetic therapy.

SUMMARY OF THE INVENTION

It is thus the purpose of the present invention to provide useful and cost effective cosmetic compositions comprising inter alia small magnetic particles, characterized by magnetic field adapted to be topically administrated on the skin. Most preferably, the aforementioned magnetic particles are obtained from the salts of the Dead Sea. Additionally or alternatively, the said magnetic particles are selected from iron, $Fe_2O_3$ or any other ferromagnetic element or compound, or optionally selected from nickel, cobalt, neodymium, samarium or any mixture thereof.

It is in the scope of the present invention wherein the cosmetic compositions defined above are in the form of creams, gels, lotions, masks, ointments, foams, soaps, shampoos, bath salts or aromatic oils. Those magnetic particles are solubilized, dispersed or suspended in waterborne or solvent-base emulsions, solutions or any combination thereof.

It is also in the scope of the present invention wherein the cosmetic compositions defined above comprising additives. Those additives are selected yet not limited to antioxidants; vitamins, such as A, C, or E; medically active agents; chemo-therapeutic agents; radio-therapeutic agents; humidifiers; biocides; pigments; smell agents; odorants; colorants; UV absorbents and/or UV blockage agents such titanium oxide, zinc oxide etc.; polymers, e.g. also monomers, oligomers and co-polymers; thickeners; co-solvents; emulsifiers; surfactants or vegetable extracts, such as Aloe Vera extract. Those cosmetic compositions may be selected from, yet not limited to anti-aging magnetic head/neck wrap or anti-aging facial mask Moreover; those cosmetic compositions are possibly suspended in polyalkylsiloxane, as such as polymethylsiloxane.

It is still in the scope of the present invention wherein the magnetic particles are characterized as nano-magnetic particles, and hence ranges from 2 to 20 nm in maximum diameter and/or form 20 to 200 nano-meter in diameter.

Lastly, it is yet in the scope of the present invention wherein the magnetic particles as defined in any of the above, are provided as an external layer of bandages, dressings, compresses or warps, so constantly approached to be in an intimate contact with the patient's skin.

DETAILED DESCRIPTION OF THE INVENTION

The following description is provided, along all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide for cosmetic compositions comprising inter alia small magnetic particles.

Various cosmetic preparations have been made to provide the magnetic compositions useful in a wide range of products and cosmetic treatments. Those compositions are selected, yet at any means not limited to cosmetic compositions in the form of creams, gels, lotions, masks, ointments, foams, soaps, shampoos, bath salts or aromatic oils.

More specifically, those compositions are especially useful for the preparation of cosmetic compositions comprising inter alia magnetic particles, particularly nano-powders of said magnetic particles, of various types and mixtures, especially salts, mud, pure substances and compositions produced or obtained from the Dead Sea.

It is further in the core of the present invention, wherein the aforementioned cosmetic compositions are the form selected, yet not limited to at least one of the group of Dead Sea bath salts; Dead Sea mineral mud; hydrophilic gels; lipophilic gels; protective dermatological ointments; ointments in emulsions; dermatological anhydrous pastes; dermatological tinctures; nourishing face creams; nourishing face cream in emulsions; moisturizing face creams; moisturizing face creams; moisturizing face cream in emulsions; moisturizing face gels; hair and scalp conditioning mask or scalp treatment shampoos.

It is acknowledged in this respect that the present invention is especially related to magnetic compositions in the form of emulsions. The term emulsion is referring any non-ideal phase comprising of micelles of any size or type, reversed micelles, a multi-phase compartmentability, water-in-oil (W/O) emulsions, oil-in-water (O/W) emulsions, water-in-oil-in water (W/O/W), oil-in-water-in-oil (O/W/O) or any combination thereof.

In order to understand the invention and to see how it may be carried out in practice, some 12 preferred embodiments will now be described, by way of non-limiting example only, with reference to the accompanying examples as follows:

EXAMPLE 1

Dead Sea bath salt was prepared. Said salt mixture comprising the ingredients as described in table 1 and table 2:

TABLE 1

Major constituents of the Dead Sea salt, utilized also for the preparation of the Dead Sea bath salt product.

| MAJOR CONSTITUENTS | FORMULA | PERCENT IN DRY MATTER |
|---|---|---|
| MAGNESIUM | (MgCl2) | 30.0-34.0% |
| SODIUM CHLORIDE | (NaCl) | 8.0-18.0% |
| POTASSIUM CHLORIDE | (KCl) | 22.0-28.0% |
| CALCIUM CHLORIDE | (CaCl2) | 00.3-00.7% |
| SULFATES | (SO4) | 00.1-00.2% |
| BROMIDES | (Br) | 00.2-00.4% |
| INSOLUBLE MATTER | | 00.2-00.9% |
| SILICATES | (SIO2) | 00.1-00.2% |

TABLE 2

Minor constituents of the Dead Sea salt, utilized also for the preparation of the Dead Sea bath salt product

| MANOR CONSTITUENTS | SIGN | PERCENT IN DRY MATTER |
|---|---|---|
| RUBIDIUM | (Rb) | 300-400 ppm |
| PHOSPHATES | (PO4) | 50-60 ppm |
| IRON | (Fe) | 20-40 ppm |
| STRONTIUM | (Si) | 100-200 ppm |
| BORON | (BO3) | 5-10 ppm |
| LITHIUM | (Li) | 2-4 ppm |
| MANGANESE | (Mn) | 2-4 ppm |
| ALUMINUM | (Al) | 5-10 ppm |
| CESIUM | (Cs) | 1-2 ppm |

EXAMPLE 2

Dead Sea mineral mud was prepared. Said mud mixture comprising the clays as described in table 2 and table 3:

TABLE 3

Semi quantitative mineralogical composition of the clay (less then 2 micrometer), fraction (%) of Dead Sea mud.

| Mineralogical composition | Fraction (%) of Dead Sea Mud. |
|---|---|
| Illite - semectite phases | 50-70% |
| Kaolinite | 10-20% |
| Illite | 10-15% |
| Calcite | 5-15% |
| Quartz | 1-5% |
| Chlorite | less then 5% |
| Palygorskite | less then 5% |

These results are a summary of XRD analysis of two separate aliquots of the same sample of crude mineral mud. One was analyzed after washing with distilled water and the second was analyzed after treatment with diluted HCl and $H_2O_2$.

TABLE 4

Elemental chemical analysis performed by inductive coupled plasma (ICP) method and wet analytical analysis methods:

| Elements | Content in PPM | Elements | Content in PPM |
|---|---|---|---|
| Si | 107,500 | V | 45 |
| Ca | 105,300 | Ni | 25 |
| Cl | 40,500 | Li | 17 |
| Fe | 24,500 | Cu | 11 |
| Al | 22,500 | Co | 7 |
| Mg | 18,600 | Pb | 5 |
| Ti | 2,700 | Th | 4 |
| P | 1,300 | As | 2.5 |
| S | 1,200 | U | 2.3 |
| Br | 1,200 | Mo | 1.5 |
| Sr | 400 | Sn | 1 |
| Mn | 225 | Ag | <1 |
| Ba | 200 | Cd | 0.6 |
| Cr | 58 | Be | 0.5 |
| Zn | 48 | Sb | 0.2 |

Magnetic nano compositions are selected, yet not limited to the group consisting of soft ferrite particles or ferroaluminates, such as Magnetite ($Fe_3O_4$), barium hexaferrite, strontium hexaferrite, undoped barium hexaferrite, undoped strontium hexaferrite, manganese zinc ferrite. Those compositions are dispersed in a cosmetic preparation in the demagnetized state and the preparation is magnetized after cosmetic application to the skin. In the following examples, all percents are by weight and are based upon the total composition weight.

EXAMPLE 3

A hydrophilic gel was prepared. The gel comprising a suspension of magnetically hard magnetite nano powders. Magnetic hard compositions selected from magnetite, Dead Sea bath salt, Dead Sea minerals, Dead Sea Mud or a mixture thereof, characterized by an average particle size ranges from 50 to 200 μm, 10% (wt) was admixed to a mixture of 20% propylene glycol, 20% glycerol, 1%; hydroxypropyl cellulose and 54.0% distilled water. The obtained mixture was homogenized by a means of a Silverson homogenizer at 15,000 rpm for about 30 min.

EXAMPLE 4

A lipophilic gel was prepared. The gel comprising a suspension of magnetically hard magnetite nano powders. Magnetic hard compositions selected from magnetite, Dead Sea bath salt, Dead Sea minerals, Dead Sea Mud or a mixture thereof, characterized by an average particle size ranges from 50 to 200 nm, 10% (wt) was admixed to a mixture of 10% Quaternium-18 Hectorite, 10% propylene carbonate and 70% caprylic/capric triglyceride. The obtained mixture was homogenized by a means of a Silverson homogenizer at 15,000 rpm for about 30 min.

EXAMPLE 5

A protective dermatological ointment in water-in-oil (W/O) emulsion was prepared. The following ingredients were thoroughly admixed in one organic phase heated to 65° C.: sorbitan isostearate, 2.5%; petrolatum, 20%; synthetic lanolin, 3.5% and mineral oil, 25% at 25° C., 7.5%. In a second step, a water-miscible phase was thoroughly admixed by a means of a Silverson homogenizer at 5,000 rpm for about 10 min at 65° C. This solution comprises of glycerol, 4.0%; de-ionized water, up to 100% and Dead Sea salt, 1.0%. Subsequently, the homogenized solution obtained above was cooled to 30° C., and magnetic hard compositions selected from magnetite, Dead Sea bath salt, Dead Sea minerals, Dead Sea mud or a mixture thereof, 2.0% was thoroughly admixed.

It is acknowledged in this respect that various derivatives of the following formulation were found useful. For example, the aforementioned magnetite ingredient was admixed in the form of either water-miscible or water-immiscible nano-suspension gel, as defined in example No. 3 and 4, wherein magnetic composition powder, 20% is used.

EXAMPLE 6

A dermatological anhydrous paste was prepared. The following ingredients were thoroughly admixed in one organic phase heated to 65° C.: petrolatum, up to 100%; synthetic lanolin, 5.0%; jojoba oil, 15.0% and myristyl myristate, 3.0%. In a second step, a water-miscible phase was thoroughly admixed by a means of a Silverson homogenizer at 5,000 rpm for about 10 min at 65° C. This solution comprises of glycerol, 4.0%; de-ionized water, up to 100% and Dead Sea salt, 1.0%. Subsequently, the homogenized solution obtained above was cooled to 30° C., and magnetic hard compositions selected from magnetite, Dead Sea bath salt, Dead Sea minerals, Dead Sea mud or a mixture thereof, 1.0% was thoroughly admixed.

EXAMPLE 7

A dermatological tincture was prepared. The following ingredients were thoroughly admixed in one water miscible phase heated at ambient temperature: butylene glycol, 5%; propylene glycol, 5%; de-ionised water, up to 100% and magnetic hard compositions selected from magnetite, Dead Sea bath salt, Dead Sea minerals, Dead Sea mud or a mixture thereof, 1 to 20%

EXAMPLE 8

A nourishing face cream in W/O emulsion was prepared. It is acknowledge in this respect that any emulsion is suitable for said preparation, including W/O, O/W, W/O/W and O/W/O emulsions, wherein the W/O emulsion provided hereto and below in a non-limiting manner as one possible example. The following ingredients were thoroughly admixed in one organic phase at 30° C.: cetyl PEG/PPG-10/11 dimethicone, 2.0%; Polyglyceryl-4-Isostearate, 0.5%; isohexadecane, 18.0%; caprylic/capric triglyceride, 2.0%; butyrospermum parkii, 2.0%; isopropyl myristate, 2.0%; phenoxyethanol & methylparaben & butyl paraben & ethylparaben & propylparaben, 0.5%. In a second step, a water-miscible phase was thoroughly admixed by a means of a Silverson homogenizer at 5,000 rpm for about 10 min. at 30° C. This solution comprises of deionised water, up to 100%; glycerin, 4.0%; Dead Sea Water, 2.0%. Subsequently, the homogenized solution obtained above was cooled to 30° C., and magnetic hard compositions selected from magnetite, Dead Sea bath salt, Dead Sea minerals, Dead Sea mud or a mixture thereof, 5.0% was thoroughly admixed by a slow stirring.

EXAMPLE 9

Moisturizing face cream in W/O emulsion was prepared. The following ingredients were thoroughly admixed in one organic phase at 75° C.: deionised water, up to 100%; propylene glycol, 2%; glycerin, 1%; methylparaben, 0.1%; imidazolidinyl urea, 0.1%; Dead Sea salt & water (Dead Sea water), 0.5%. In a second step, a water-miscible phase was thoroughly admixed by a means of a silverson homogenizer at 5,000 rpm for about 10 min. at 75° C. This solution comprises of ethyhexyl palmitate, 6.0%; isopropyl myristate, 3.0%; glyceryl stearate, 3.0%; cetyl alcohol, 2.0%; PEG-40; stearate, 1.0%; sorbitan tristearate, 0.5%; dimethicone, 0.5%; propylparaben, 0.2%; fragrance, qs. Subsequently, the homogenized solution obtained above was cooled to 30° C., and magnetic hard compositions selected from magnetite, Dead Sea bath salt, Dead Sea minerals, Dead Sea mud or a mixture thereof, 5.0% was thoroughly admixed by a slow stirring.

EXAMPLE 10

Moisturizing face gel was prepared. The following ingredients were thoroughly admixed in one organic phase: deionised water, up to 100%; xanthan gum, 0.6%; hydroxyethylcellulose, 0.6%; methylparaben, 0.1%; imidazolidinyl urea, 0.1%; propylene, 3.5%; glycerol, 4.0%; fragrance, qs. The water, xanthan gum and hydroxyethylcellulose are homogenized at ambient temperature. The remaining raw materials are added in order, with stirring. In a second step, a water-miscible phase was thoroughly admixed by a means of a Silverson homogenizer at 5,000 rpm for about 10 min. at 75° C. This solution comprises of ethyhexyl palmitate, 6.0%; isopropyl myristate, 3.0%; glyceryl stearate, 3.0%; cetyl alcohol, 2.0%; PEG-40; stearate, 1.0%; sorbitan tristearate, 0.5%; dimethicone, 0.5%; propylparaben, 0.2%; fragrance, qs. Subsequently, the homogenized solution obtained above was cooled to 30° C., and magnetic hard compositions selected from magnetite, Dead Sea bath salt, Dead Sea minerals, Dead Sea mud or a mixture thereof, 1.0% was thoroughly admixed by a slow stirring.

EXAMPLE 11

Hair and scalp conditioning mask was prepared. The following ingredients were thoroughly admixed in one organic phase at 75° C.: deionised water, up to 100%; stearalkonium chloride, 6.0%; lycerin, 4.0%; and lactic acid, 0.3%. In a second step, a water-miscible phase was thoroughly admixed by a means of a Silverson homogenizer at 5,000 rpm for about 10 min. at 75° C. This solution comprises cetyl alcohol, 3.0%; oleyl alcohol, 2.0%; jojoba oil, 4.0%, glyceryl stearate, PEG-100 stearate, 3.0%; and dimethicone, 0.5%. Subsequently, the homogenized solution obtained above was cooled to 30° C., and magnetic hard compositions selected from magnetite, Dead Sea bath salt, Dead Sea minerals, Dead Sea mud or a mixture thereof, 5.0% was thoroughly admixed by a slow stirring.

EXAMPLE 12

Scalp treatment shampoo was prepared. The following ingredients were thoroughly admixed in one organic phase: deionised water, up to 100%; xanthan gum, 0.6%; magnesium aluminum silicate, 0.6%; methylparaben, 0.1%; imidazolidinyl urea, 0.1%; sodium laureth sulfates 8.0%; ammonium lauryl sulfate, 5.0%; lauramide DEA, 2.0%; fragrance, qs. The water, xanthan gum and magnesium aluminum silicate are homogenized at room temperature. The remaining raw materials are added in order, with stirring. In a second step, a water-miscible phase was thoroughly admixed by a means of a Silverson homogenizer at 5,000 rpm for about 10 min at 75° C. This solution comprises cetyl alcohol, 3.0%; oleyl alcohol, 2.0%; jojoba oil, 4.0%, glyceryl stearate, PEG-100 stearate, 3.0%; and dimethicone, 0.5%. Subsequently, the homogenized solution obtained above was cooled to 30° C., and magnetic hard compositions selected from magnetite, Dead Sea bath salt, Dead Sea minerals, Dead Sea mud or a mixture thereof, 1.0% was thoroughly admixed by a slow stirring.

The invention claimed is:

1. A cosmetic preparation for topical application onto skin of a subject, the preparation consisting of:
   Dead Sea mud;
   1 wt % demagnetized strontium hexaferrite nanoparticles dispersed in the mud, the demagnetized nanoparticles being suitable for magnetization when applied to the skin of the subject, wherein the demagnetized nanoparticles have a diameter from 20 to 200 nm; and
   one or more cosmetically acceptable additives selected from the group consisting of an antioxidant, a vitamin, a chemotherapeutic agent, a radio therapeutic agent, a humidifier, a biocide, a pigment, a smell agent, an odorant, a colorant, a UV absorbent, a UV blockage agent, a co-solvent, propylene glycol, glycerol, hydroxypropyl cellulose, distilled water, quaternium-18 hectorite, propylene carbonate, caprylic/capric triglyceride, sorbitan isostearate, petrolatum, synthetic lanolin, mineral oil, jojoba oil, myristyl myristate, butylenes glycol, propylene glycol, cetyl PEG/PPG-10/11 dimethicone, polyglyceryl-4-isostearate, isohexadecane, butryospermum parkii, isopropyl myristate, phenoxyethanol, methylparaben, butylparaben, ethylparaben, propylparaben, glycerin, imidazolidinyl urea, ethyhexyl palmitate, glyceryl stearate, cetyl alcohol, PEG-40 stearate, sorbitan tristearate, dimethicone, fragrance, xanthan gum, hydroxyethyl cellulose, propylene, stearalkonium chloride, lactic acid, oleyl alcohol, PEG-100 stearate, magnesium aluminum silicate, sodium laureth sulfates, ammonium lauryl sulfate, and lauramide DEA.

2. The cosmetic preparation according to claim 1, wherein the demagnetized nanoparticles are included in a composition selected from the group consisting of a cream, a gel, a lotion, a mask, an ointment, an emulsion, a foam, a soap, a shampoo, a bath salt and an aromatic oil.

3. The cosmetic preparation according to claim 1, being in a form selected from the group consisting of a Dead Sea bath salt, a Dead Sea mineral mud, a hydrophilic gel, a lipophilic gel, a protective dermatological ointment, an ointment in water-in-oil (W/O) emulsion, a dermatological anhydrous paste, a dermatological tincture, a nourishing face cream, a nourishing face cream in W/O emulsion, a moisturizing face cream, a moisturizing face cream in W/O emulsion, a moisturizing face gel, a hair and scalp conditioning mask and a scalp treatment shampoo.

4. The cosmetic preparation according to claim 1, wherein the diameter range is from 50 to 200 nm.

5. A cosmetic preparation, consisting of:
   Dead Sea mud;
   1 wt % demagnetized strontium hexaferrite nanoparticles dispersed in the mud, the demagnetized nanoparticles being suitable for magnetization when applied to skin of a subject, wherein the demagnetized nanoparticles have a diameter from 20 to 200 nm; and
   one or more cosmetically acceptable additives selected from the group consisting of an antioxidant, a vitamin, a chemotherapeutic agent, a radio therapeutic agent, a humidifier, a biocide, a pigment, a smell agent, an odorant, a colorant, a UV absorbent, a UV blockage agent, a co-solvent, propylene glycol, glycerol, hydroxypropyl cellulose, distilled water, quaternium-18 hectorite, propylene carbonate, caprylic/capric triglyceride, sorbitan isostearate, petrolatum, synthetic lanolin, mineral oil, jojoba oil, myristyl myristate, butylenes glycol, propylene glycol, cetyl PEG/PPG-10/11 dimethicone, polyglyceryl-4-isostearate, isohexadecane, butryospermum parkii, isopropyl myristate, phenoxyethanol, methylparaben, butylparaben, ethylparaben, propylparaben, glycerin, imidazolidinyl urea, ethylhexyl palmitate, glyceryl stearate, cetyl alcohol, PEG-40 stearate, sorbitan tristearate, dimethicone, fragrance, xanthan gum, hydroxyethyl cellulose, propylene, stearalkonium chloride, lactic acid, oleyl alcohol, PEG-100 stearate, magnesium aluminum silicate, sodium laureth sulfates, ammonium lauryl sulfate, and lauramide DEA.

* * * * *